United States Patent [19]

Tiffany

[11] Patent Number: 4,610,690

[45] Date of Patent: Sep. 9, 1986

[54] RUPTURE RESISTANT PROSTHESIS WITH BONDED SURFACE LAYER AND METHOD OF FORMING SAME

[75] Inventor: John S. Tiffany, Ventura, Calif.

[73] Assignee: Mentor Corporation, Minneapolis, Minn.

[21] Appl. No.: 468,249

[22] Filed: Feb. 22, 1983

[51] Int. Cl.$^4$ ............................................... A61F 2/12
[52] U.S. Cl. ...................................................... 623/8
[58] Field of Search ...................... 3/36, 1; 128/335 R, 128/156, 155; 604/849

[56] References Cited

U.S. PATENT DOCUMENTS

| | | | |
|---|---|---|---|
| 3,559,214 | 2/1971 | Pangman | 3/36 |
| 3,600,718 | 8/1971 | Boone | 3/36 |
| 3,919,724 | 11/1975 | Sanders et al. | 3/36 |
| 3,975,350 | 8/1976 | Hudgin et al. | 3/1 |
| 4,173,606 | 11/1979 | Stoy et al. | 3/1 |
| 4,208,506 | 6/1980 | Deichert et al. | 3/1 |
| 4,286,341 | 9/1981 | Greer et al. | 3/1 |
| 4,377,010 | 3/1983 | Fydelor et al. | 3/1 |
| 4,455,691 | 6/1984 | Van Aken Redinger | 3/36 |

Primary Examiner—Richard J. Apley
Assistant Examiner—David J. Isabella
Attorney, Agent, or Firm—Kinney & Lange

[57] ABSTRACT

A surgically implantable prosthesis such as a mammary implant, that is rendered rupture-resistant by a lubricious layer bonded to the inner surface, outer surface, or both such surfaces of a wall of a flexible, creasable shell of the prosthesis. The lubricious layer reduces self-abrasion damage between sliding surfaces of the shell in a folding or creased area of the shell after surgical implantation. The lubricious layer can be mechanically bonded, such as through physical locking within an interpenetrating lattice structure of such wall, or can be attached to the shell's wall through a covalent chemical bond. An example of the rupture-resistant prosthesis includes a lubricious layer of an acrylamide polymer radiation bonded to at least one wall surface of a silicone shell or bag.

25 Claims, 6 Drawing Figures

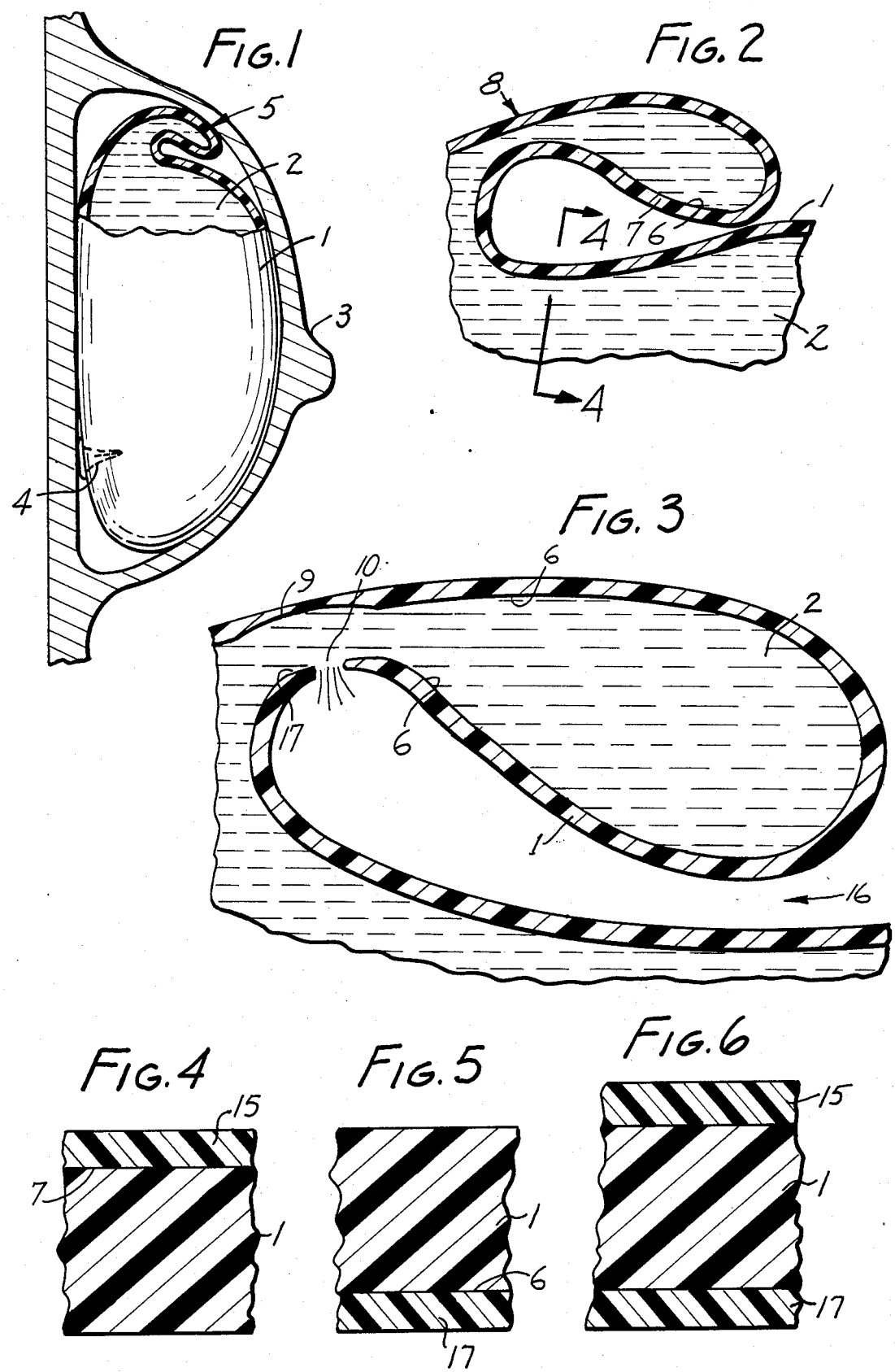

RUPTURE RESISTANT PROSTHESIS WITH BONDED SURFACE LAYER AND METHOD OF FORMING SAME

BACKGROUND OF THE INVENTION

Surgically implanted flexible bag-type mammary prostheses have suffered a serious problem with the bag rupturing in certain cases after surgical implantation. This is believed to occur more frequently when the bag develops a crease; however, several theories have been advanced to explain just why such a bag ruptures. Some believe it is due to the stress differential between inner and outer surfaces of a bag wall section and a crease area caused by one wall surface being in compression and the other being in tension. Others believe that this is caused by a change in the physical properties such as modulus, etc., over a prolonged period of maintaining a crease. Still others believe that the bag failures to be caused at least in part by friction between opposing wall sections in a fold area. This latter view is explained in Rees et al. in "The Use of Inflatable Breast Implants," *Plastic and Reconstructive surgery*, Volume 52, Number 6, December 1973, pp. 609–615. It has been known for many years that in some surgical implantations of a flexible shell or bag containing an inflatable liquid, such as normal saline, rupture occurs at a crease area, perhaps many months or years after surgical implantation. This type of bag wall failure is known as "fold flaw." Many theories as to the mechanism of such failure have been proposed, but heretofore there has been no solution to such recognized problem.

In a copending application Ser. No. 350,916 filed Feb. 22, 1982 many of the possible contributing factors for the rupture of these prostheses are described, pointing out that the self-abrasion injury to the bag wall was the dominant mechanism. That patent application discloses a method of reducing the rupture of the prosthesis by injecting an inflating liquid, such as normal saline, containing a uniform dispersion of lubricious polymer particles in such liquid. These particles act as a lubricant between two inner surface areas that periodically slide against each other in a crease area of the prosthesis bag.

SUMMARY OF THE INVENTION

In accordance with the present invention, disclosed is a rupture-resistant prosthesis having a flexible creasable shell adapted to contain an inflating liquid and having a wall with inner and outer surfaces, an abrasion-resistant layer having substantially greater lubricity than the shell bonded to at least one of such wall surfaces. The abrasion-resistant layer substantially reduces self-abrasion damage to the shell wall during sliding contact between opposing areas of this surface when liquid is confined within the shell, and particularly when the shell has a crease after surgical implantation. In accordance with one embodiment of the present invention, bonding can be achieved by mechanically locking the lubricious layer into the pores or interpenetrating the lattice structure of the prosthesis. Alternatively, the abrasion-resistant layer is chemically bonded through a covalent bond, such as occurs in radiation grafting.

BRIEF DESCRIPTION OF THE DRAWINGS

FIG. 1 is a schematic sectional view of a human breast which has been surgically implanted with a mammary prosthesis that has developed a fold;

FIG. 2 is an enlarged fragmentary view in section of the fold area of the prosthesis of FIG. 1 prior to rupture;

FIG. 3 is still a further enlarged view similar to FIG. 2, but showing the prosthesis after rupture;

FIG. 4 is an enlarged sectional view taken along line 4—4 showing the lubricious layer on an outer surface of the prosthesis bag;

FIG. 5 is a view similar to FIG. 4, but alternatively showing the lubricious layer on an inner surface of the bag;

FIG. 6 is a view similar to FIGS. 4 and 5, but alternatively showing the lubricious layer on both inner and outer surfaces of the bag.

DETAILED DESCRIPTION OF THE PREFERRED EMBODIMENT

In accordance with the present invention, it has been found that securing a lubricious layer to the surface of an inflatable prosthesis advantageously renders the prosthesis resistant to rupturing after implantation.

A mammary prosthesis is shown in FIG. 1 having a flexible, creasable shell 1 with an inflating fluid 2 which has been surgically implanted within a breast 3 of a patient. A filling valve 4 is schematically shown at a rear of the prosthesis. A crease area, generally shown at 5 is shown at an upper portion of the prosthesis in FIG. 1. As previously explained, this phenomena has been known for years as the "fold flaw" problem because the shell 1 tended to rupture at this folded or creased area, perhaps many months or years after surgical implantation.

As shown in the enlarged view of FIG. 2, the prosthesis with wall 1, sometimes known as the "bag," has an inner surface 6 and an outer surface 7. Portions of inner surface 6 are shown contacting each other in an area shown generally at 8, but no rupture has occurred.

In the further enlarged view of FIG. 3, a thinned area 9 has occurred by abrasive wearing from an inner surface of the bag's wall 1. However, no breakthrough has yet occurred at 9. In opposing portion, a break has occurred at 10 due to abrasive wearing, and thus liquid 2 drains from the bag. Rupture of the bag is highly undesirable because it permits the liquid to come in direct contact with body tissue where it can shift and be absorbed into the body. Rupture of the bag also destroys the shape in profile of the bag.

In accordance with one embodiment of the present invention, the "fold flaw" rupture problem illustrated in FIG. 3 is greatly reduced by bonding a lubricious layer 17 to an inner surface of bag wall 1, as shown in FIG. 5. In many mammary prostheses, the bag wall 1 is of silicone polymer and provides the strength, flexibility, and other necessary properties to reliably confine the inflating liquid, except where a fold flaw rupture occurs. Because of the physical supporting nature of the bag wall 1, which can be of a thickness from about 0.003 to about 0.050 inches, the lubricious layer 17 can be much thinner, such as from about 0.0001 to about 0.005 inches. The lubricious layer 17 can also be selected with less regard to its necessary property to physically contain the inflating liquid. Instead, the lubricious layer 17 is selected for its bonding and lubricious properties. It does not require a large degree of tensile strength, because the silicone polymer wall 1 provides this property for the bag.

When the fold or crease in a bag causes two portions of the external surface of the bag to periodically rub together, such as at the location generally shown at 16 in FIG. 3, the outer surface of bag wall 1 advantageously is covered with the lubricious layer. Thus, when the outer surface abrading occurs, the chance of rupture is substantially reduced by including a lubricious layer 15 bonded to an outer surface of the bag wall as shown in FIG. 4.

In accordance with the most preferred embodiment of the present invention, the silicone polymer bag wall has lubricious layers bonded to inner and outer surfaces as shown in FIG. 6. Thus, regardless of the particular configuration of the crease, two contacting surfaces will always have contacting lubricious layers.

It is important that the lubricious layers 15 and 17 are bonded to the supporting bag wall 1 so that as the bag flexes as a result of patient movement, the layer does not simply rub off and abrasion on the bag wall continue to rupture to the rupture point, as depicted in FIG. 3. It should be understood that over a period of several years the liquid inside the bag, as well as the patient's body fluids outside the bag, could have a washing or flushing effect on any lubricant that was simply coated on the bag without such bonding. For example, the prosthesis could not be dip coated in a biocompatible lubricant immediately prior to surgical implantation. After a period of time, the coating would rub off.

In accordance with the present invention, the bonding necessary to secure the lubricious layer to the supporting bag wall, such as a silicon polymer, is of several different types. One form of bonding includes a mechanical bond in which layer 15 or 17 is forced into an interpenetrating lattice structure of the bag wall 1. Layers 15 or 17 would be difficult to remove because such removal would require fracturing fingers or portions of these layers that were intertwined in the lattice structure of supporting bag wall 1.

In accordance with an alternative embodiment of the present invention, lubricious layer 15 or 17 is chemically bonded to supporting wall 1 covalently. Many known chemical procedures could be used to create such covalent bonding, some of which are described in *Synthetic Biomedical Polymers: Concepts and Applications:* M. Szycher and W. J. Robinson, Eds. (1980) pp 133-151. Alternatively, the bond could be a combination of the mechanical interpenetrating type and the chemical covalent bond type.

In accordance with one embodiment of the present invention, a silicone layer is exposed to high-energy radiation, such as gamma rays from a cobalt-60 source. I have found that 2.5 megarads of gamma irradiation is effective, and is thus preferred. The irradiated layer is then immersed in an aqueous monomer solution containing a monomer capable of forming a lubricious layer on the silicone bag. In accordance with the present invention, the thickness of the resulting lubricious hydrogel graft is dependent on the time, temperature, and pH of the reaction. Preferably, the silicone bag is immersed in a hydrogel solution at a temperature of from about 30° C. to about 90° C. for about 1 to about 4 hours. The reaction is preferably conducted in a pH range of from about 2 to about 6, and most preferably at a pH of about 3. Incorporation of ferrous sulfate into this hydrogel monomer solution prevents formation of hydroperoxides.

In accordance with an alternate embodiment of the present invention, the silicone is exposed to gaseous ozone and then treated with the monomer solution as described above. This has the benefit of treating only the surface, rather than the whole bulk of the silicone, as occurs with radiation.

In accordance with the present invention, the lubricious layers 15 and 17 are formed on the surface of the creasable shell by immersion into a variety of monomers. Illustrative hydrogel-forming monomers include but not limited to vinylpyrrolidone; acrylamide; methacrylamide; N-substituted acrylamide; and hydroxyalkyl methacrylates such as hydroxyethyl methacrylate, glyceryl methacrylate, hydroxypropyl methacrylate, and the like; and their biologically compatible copolymers. In accordance with a preferred embodiment of the present invention, the monomers include vinylpyrrolidone, acrylamide, and hydroxyethyl methacrylate.

In accordance with the present invention, grafting of hydrogels to a silicone bag prosthesis has produced prostheses having substantially rupture-resistant lubricious layers. A hydrogel-grafted silicone composite has been tested for its abrasion-resistance by reciprocally rubbing a piece of the composite material against a "fold" in a similar piece of material in a fluid (saline) medium. Under a controlled rate and applied force, an untreated sample of platinum-cured silicone will typically abrade through in about 70,000 cycles, whereas a hydrogel-grafted silicone composite is resistant to abrasion for more than two million cycles.

In one embodiment of the present invention, the construction of the rupture-resistant prosthesis involves bonding a lubricious layer of acrylamide to the silicone polymer supporting bag wall having substantially less lubricious properties than the acrylamide. This bonding is done by subjecting the silicone polymer to electron radiation in the presence of oxygen and later graft polymerizing the acrylamide to the silicone polymer as described above.

Once the lubricious layers have been applied to both inner and outer surfaces of the bag in the preferred embodiment, the bag is inflated and sealed prior to surgical implantation. Alternatively, the bag with its lubricious layers is inflated at the time of surgical implantation. This is often done by injecting normal saline into the bag during surgery.

Although the present invention has been described in detail and with reference to its preferred embodiments, it is understood by those skilled in the art that modifications can be made thereto without departure from the spirit and scope thereof.

I claim:

1. A surgically implantable rupture-resistant breast prosthesis comprising:
    a flexible, creasable shell of silicone polymer adapted to contain a saline inflating liquid and having a wall with inner and outer surfaces; and
    an abrasion resistant hydrogel layer having substantially greater lubricity than the shell bonded to one of such wall surfaces to substantially reduce self-abrasion damage to the shell wall during sliding contact between opposing areas of this one surface when a saline inflating liquid is confined within the shell and the shell wall has a crease after surgical implantation.

2. A rupture-resistant prosthesis as set forth in claim 1, wherein the abrasion-resistant layer is bonded to the shell's inner surface.

3. A rupture-resistant prosthesis as set forth in claim 1, wherein the abrasion-resistant layer is bonded to the shell's outer surface.

4. A rupture-resistant prosthesis as set forth in claim 1, wherein there are abrasion-resistant layers bonded to both the inner and outer surfaces of the shell.

5. A rupture-resistant prosthesis as set forth in claim 1, wherein the abrasion-resistant layer is bonded to the one surface by a mechanical bond.

6. A rupture-resistant prosthesis as set forth in claim 5, wherein the mechanical bond includes a physical locking within an interpenetrated lattice structure.

7. A rupture-resistant prosthesis as set forth in claim 1, wherein the abrasion-resistant layer is bonded to the one surface by a chemical bond.

8. A rupture-resistant prosthesis as set forth in claim 7, wherein the chemical bond is a covalent bond.

9. A rupture-resistant prosthesis as set forth in claim 7, wherein the bond is a graft polymerization bond.

10. A rupture-resistant prosthesis as set forth in claim 1, wherein the abrasion-resistant layer is selected from the group consisting of acrylamide, vinylpyrrolidone, and hydroxymethyl methacrylate.

11. A rupture-resistant prosthesis as set forth in claim 1, wherein the shell is in an unfilled state prior to surgical inflation.

12. A rupture-resistant prosthesis, as set forth in claim 1, wherein the shell is prefilled with a saline inflating liquid prior to surgical implantation.

13. A rupture-resistant prosthesis as set forth in claim 13, wherein the inflating liquid is biocompatible.

14. A rupture-resistant prosthesis as set forth in claim 1, wherein the shell wall has a thickness of from about 0.003 to about 0.050 inch.

15. A rupture-resistant prosthesis as set forth in claim 1, wherein the abrasion-resistant layer has a thickness from about 0.0001 to about 0.005 inch.

16. A rupture-resistant prosthesis as set forth in claim 1, wherein the abrasion-resistant layer is biocompatible.

17. A rupture-resistant prosthesis as set forth in claim 1, wherein the abrasion resistant hydrogel layer is selected from the group consisting of vinylpyrrolidone, acrylamide, methacrylamide, N-substituted acrylamide and hydroxyalkyl methacrylate.

18. A surgically implantable rupture-resistant breast prosthesis comprising:
a flexible, creasable shell of silicone polymer adapted to contain a saline inflating liquid and having a wall with inner and outer surfaces; and
an abrasion-resistant hydrogel layer selected from the group consisting of acrylamide, vinylpyrrolidone, methacrylamide, N-substituted acrylamide and hdyroxymethyl methacrylate mechanically or chemically bonded to one of such wall surfaces to substantially reduce self-abrasion damage to the shell wall during sliding contact between opposing areas of this one surface when a saline inflating liquid is confined within the shell and the shell wall has a crease after surgical implantation.

19. A rupture-resistant breast prosthesis according to claim 18, wherein the abrasion-resistant hydrogel layer is selected from the group consisting of acrylamide, vinylpyrrolidone and hydroxymethyl methacrylate.

20. A method of forming a surgically implantable rupture-resistant breast prosthesis comprising:
(a) forming an unfilled flexible creasable shell of silicone polymer with a wall having inner and outer surfaces; and
(b) mechanically or chemically bonding to one of such wall surfaces an abrasion resistant hydrogel layer having substantially greater lubricity than the shell, whereby the shell can be inflated with a saline inflating liquid and surgically implanted to substantially reduce self-abrasion damage to the shell during sliding contact between opposing areas of this one surface when a saline inflating liquid is confined within the shell and the shell wall has a crease after surgical implantation.

21. A method of forming a rupture-resistant prosthesis as set forth in claim 20, wherein the shell is inflated and sealed during surgical implantation.

22. A method of forming a rupture-resistant prosthesis as set forth in claim 20, wherein the shell is prefilled with a saline inflating liquid and sealed prior to surgical implantation.

23. A method of forming a rupture-resistant prosthesis as set forth in claim 20, wherein the bonding step includes bonding an abrasive-resistant layer to both inner and outer surfaces of the shell wall.

24. A method of forming a rupture-resistant prosthesis as set forth in claim 20, wherein the shell is a silicone polymer, the abrasion-resistant layer is selected from the group consisting of acrylamide, vinylpyrrolidone, and hydroxymethyl methacrylate, and the bonding is by graft polymerization.

25. A method of forming a rupture-resistant prosthesis according to claim 20, wherein the abrasion resistant hydrogel layer is selected from the group consisting of vinylpyrrolidone, acrylamide, methacrylamide, N-substituted acrylamide and hydroxyalkyl methacrylate.

* * * * *

UNITED STATES PATENT AND TRADEMARK OFFICE
CERTIFICATE OF CORRECTION

PATENT NO. : 4,610,690

DATED : September 9, 1986

INVENTOR(S) : John S. Tiffany

It is certified that error appears in the above-identified patent and that said Letters Patent is hereby corrected as shown below:

In col. 5, line 28 (claim 13), "13" should read --12--.

In col. 5, line 30 (claim 14), "1" should read --12--.

In col. 5, line 33 (claim 15), "1" should read --12--.

In col. 6, line 1 (claim 18), the word "hdyroxymethyl" should read --hydroxymethyl--.

Signed and Sealed this

Twentieth Day of January, 1987

Attest:

DONALD J. QUIGG

Attesting Officer

Commissioner of Patents and Trademarks